United States Patent [19]

Bally et al.

[11] Patent Number: 4,885,172

[45] Date of Patent: Dec. 5, 1989

[54] COMPOSITION FOR TARGETING, STORING AND LOADING OF LIPOSOMES

[75] Inventors: Marcel B. Bally; Helen Loughrey; Pieter R. Cullis, all of Vancouver, Canada

[73] Assignee: The Liposome Company, Inc., Princeton, N.J.

[21] Appl. No.: 941,913

[22] Filed: Dec. 15, 1986

Related U.S. Application Data

[63] Continuation-in-part of Ser. No. 811,037, Dec. 18, 1985, abandoned, which is a continuation-in-part of Ser. No. 749,161, Jun. 26, 1985, abandoned, which is a continuation-in-part of Ser. No. 759,419, Jul. 26, 1985.

[51] Int. Cl.$^4$ .......................... A61K 37/22; B32B 5/16; A01N 25/26; A01N 25/28
[52] U.S. Cl. .................................. 424/417; 424/450; 264/4.3
[58] Field of Search ............................... 424/417, 450

[56] References Cited

U.S. PATENT DOCUMENTS

| | | | |
|---|---|---|---|
| 4,193,983 | 3/1980 | Ullman et al. | 435/7 |
| 4,235,871 | 11/1980 | Papahadjopoulos et al. | 424/89 |
| 4,522,803 | 6/1985 | Lenk et al. | 424/1.1 |
| 4,588,578 | 5/1986 | Fountain et al. | 424/1.1 |
| 4,610,868 | 9/1986 | Fountain et al. | 435/1 |
| 4,761,288 | 8/1988 | Mezel | 424/450 |
| 4,762,720 | 8/1988 | Jizomoto | 424/450 |

FOREIGN PATENT DOCUMENTS

WO86/0432  7/1986  World Int. Prop. O.

OTHER PUBLICATIONS

Bangham, et al., Diffusion of Univalent Ions Across the Lamellae of Swollen Phospholipids. 1965, J. Mol. Biol., 13:138–252.

Papahadjopoulos, et al., Phospholipid Model Membranes I. Structural Characteristics of Hydrated Liquid Crystals, 1967, Biochim. Biophys. Acta., 135:624–638.

Wolff, et al., The Use of Monoclonal Anti-Thy$_1$ IgG$_1$ for the Targeting of Liposomes to AKR-A Cells in Vitro and in Vivo. 1984, Biochim. Biophys. Acta., 259–273.

Leserman, et al., Covalent Coupling of Monoclonal Antibodies and Protein A to Liposomes: Specific Interaction with Cells in Vitro and in Vivo, 1984, Liposom Tech. III, Gregoriadis, ed. CRC Press, pp. 29–40.

Leserman, et al., Targeting to Cells of Fluorescent Liposomes Covalently Coupled with Monoclonal Antibody or Protein A. Nature 1980, 288:602–604.

Martin, et al., Irreversible Coupling of Immunoglobulin Fragments to Preformed Vesicles, J. Biol. Chem, 257:286–288, 1982.

Martin, et al., Immunospecific Targeting of Liposomes to Cells: A Novel and Efficient Method of Covalent Attachment of Fab Fragments via Disulfide Bonds, 1981, Biochem., 20:4229–4238.

Urdal, et al., Tumor-Associated Ganglio-N-Triosylceramide, J. Biol. 1980, Chem. 255:10509–10516.

Huang, et al., Characterization of Antibody Covalently Couples to Liposomes, 1982, Biochim. Biophys. Acta., 716–140–150.

Forssen, et al., Improved Therapeutic Benefits of Doxorubicin by Engraftment in Anionic Lipsomes, 1982, Cancer Res., 43:546.

Gabizon, et al., Liposomes as in Vivo Carriers of Andriamycin: Reduced Cardiac Uptake and Preserved Antitumor Activity in Mice, 1982, Cancer Res., 42:4734.

(List continued on next page.)

*Primary Examiner*—Ronald W. Griffin
*Attorney, Agent, or Firm*—Allen Bloom; Catherine L. Kurtz

[57] ABSTRACT

The present invention describes a composition consisting of liposomes covalently or non-covalently coupled to the glycoprotein streptavidin. The streptavidin may additionally be coupled to biotinated proteins such as Immunoglobulin G or monoclonal antibodies.

The liposomes of the invention may have a transmembrane potential across their membranes, and may be dehydrated. In addition, the composition may contain ionizable bioactive agents such as antineoplastic agents, and may be used in diagnostic assays.

25 Claims, 5 Drawing Sheets

OTHER PUBLICATIONS

Rahman, et al., Doxorubicin-Induced Chronic Cardiotoxicity and Its Protection by Liposomal Administration, 1982, Cancer Res., 42:1817.

Mayer, et al., Solute Distributions and Trapping Efficiencies Observed in Freeze-Thawed Multilamellar Vesicles, 1985, Biochim. Biophys., Acta., 817:193-196.

Deamer, et al., Liposome Preparation: Methods and Mechanisms, 1983, 1N:Liposomes, Ostro M. ed., Dekker, Inc., pp. 26-51.

Hope, et al., Production of Large Unilamellar Vesicles by a Rapid Extrusion Procure. Characterization of Size Distribution, Trapped Volume and Ability to Maintain a Membrane Potential, 1985, Biochim. Biophys., Acta., 812:55-65.

Bayer, et al., On the Mode of Liposome-Cell Interactions Biotin-Conjugated Lipids as Ultrastructural Proves, 1979, Biochim. Biophys., Acta., 550:464-473.

Martin, et al., Binding Characteristics of Antibody-Bearing Liposomes, 1985, Ann. N.Y. Acad. Sci., 446:443-456.

Heath, et al., Antibody-Targeted Liposomes: Increase in Specific Toxicity of Methotrexate-Y-Aspartate, 1983, Proc. Nat'l. Acad. Sci., U.S.A. 80:1377-1381.

Bragman, et al., Simultaneous Interaction of Monoclonal Antibody-Targeted Liposomes with Two Receptors on K562 Cells, 1983, Biochim. Biophys., Acta., 730:187-195.

Bragman, et al., Cytotoxicity of Antibody-Directed Liposomes that Recognize Two Receptors on K562 Cells, 1984, JNCI, 73:127-131.

Heitzman, et al., Use of the Avidin-Biotin Complex for Specific Staining of Biological Membranes in Electron Microscopy, 1974, Proc. Nat'l. Acad. Sci., USA 71:3537-3541.

Madden, et al., Protection of Large Unilamellar Vesicles by Trehalose During Dehydration: Retention of Vesicle Contents, 1985, Biochim. Biophys., Acta., 817:67-74.

Bally, et al., Uptake of Safraine and Other Lipophilic Cations into Model Membrane Systems in Response to a Membrane Potential, 1985, Biochim. Biophys., Acta., 812:66-76.

Gregoriadis, Targeting of Drugs with Molecules, Cells and Liposomes, 1983, Trends. Pharm. Sci., 4, pp. 304-307.

Laemmli, Cleavage of Structural Proteins During the Assembly of the Head of Bacteriophage T4, 1970, Nature, 227:680-683.

Nisonoff, et al., Separation of Univalent Fragments from the Bivalent Rabbit Antibody Molecule by Reduction of Disulfide Bonds, 1960, Archives of Biochem. and Biophys., 98:230-244.

I Labelled Inulin: a Convenient Marker for Deposition of Liposomal Contents in Vivo, 1984, Biochem. and Biophys. Res. Comm., 122(1):319-324.

Goundalkar, et al., Covalent Binding of Antibodies to Liposomes Using a Novel Lipid Derivative, 1983, J. Pharm. Pharmacol., 36:465-466.

60% COUPLING

COMPOSITION FOR TARGETING, STORING AND LOADING OF LIPOSOMES

This is a continuation-in-part of copending application Ser. No. 811,037, filed Dec. 18, 1985, now abandoned, which in turn is a continuation-in-part of copending application Ser. No. 749,161, now abandoned, filed June 26, 1985, and copending application Ser. No. 759,419, filed July 26, 1985.

BACKGROUND OF THE INVENTION

The present invention is directed to liposomes. More particularly, the present invention is directed to the covalent and non-covalent coupling of liposomes to proteins for purposes of in vivo targeting, or for use in diagnostics.

Liposomes are completely closed structures composed of lipid bilayer membranes containing an encapsulated aqueous volume. Liposomes may contain many concentric lipid bilayers separated by aqueous phase (multilamellar vesicles or MLVs), or may be composed of a single membrane bilayer (unilamellar vesicles).

Liposome preparation has typically been achieved by the process of Bangham et.al., (1965 J. Mol. Biol., 13: 238-252) whereby lipids suspended in organic solvent are evaporated under reduced pressure to a dry film in a reaction vessel. An appropriate amount of aqueous phase is then added to the vessel and the mixture agitated, then allowed to stand, essentially undisturbed for a time sufficient for the multilamellar vesicles to form. The aqueous phase entrapped within the liposomes may comprise bioactive agents including, but not limited to, drugs, hormones, proteins, dyes, vitamins, or imaging agents.

The current state of the art is such that liposomes may be reproducibly prepared using a number of techniques. Liposomes resulting from some of these techniques are small unilamellar vesicles (SUVs) Papahadjopoulos and Miller, *Biochem. Biophys. Acta*, 135, p. 624-638 (1967), reverse-phase evaporation vesicles (REV) U.S. Pat. No. 4,235,871 issued Nov. 25, 1980, stable plurilamellar vesicles (SPLV) U.S. Pat. No. 4,522,803 issued June 11, 1985, and large unilamellar vesicles produced by an extrusion technique as described in copending U.S. patent application Ser. No. 788,017, filed Oct. 16, 1985, Cullis et.al., entitled "Extrusion Technique for Producing Unilamellar Vesicles", relevant portions of which are incorporated herein by reference.

One of the primary uses for liposomes is as carriers for a variety of materials, such as, drugs, cosmetics, diagnostic reagents, bioactive compounds, and the like. Such systems may be designed for both diagnostics and in vivo uses. In this regard, the ability to produce an antibody-directed vesicle would be a distinct advantage over similar undirected systems (Gregoriadis, G., *Trends Pharmacol Sci*, 4, p. 304-307, 1983). Useful applications would be in the selective targeting of cytotoxic compounds entrapped in vesicles to circulating tumor cells (Wolff et.al., *Biochim Biophys. Acta*, 802, p. 259-273 1984), or applications of these immunoglobulin-associated vesicles in the development of diagnostic assays. As is well known in the art, liposomes may be covalently coupled to proteins, antibodies and immunoglobins. Heath et.al. (*Biochim. Biophys. Acta*, 640, p. 66-81, 1981), describe the covalent attachment of immunoglobulins to liposomes containing glycosphingolipid. Leserman et. al. (*Liposome Technology, III*, 1984, CRC Press, Inc., CA., p. 29-40; *Nature*, 288, p. 602-604, 1980) and Martin et. al., (*J. Biol. Chem.*, 257, p. 286-288, 1982) have described procedures whereby thiolated IgG or protein A is covalently attached to lipid vesicles, and thiolated antibodies and Fab' fragments are attached to liposomes, respectively. These protocols and various modifications (Martin et.al, *Biochemistry*, 20, p. 4229-4238, 1981; and Goundalkar et.al., *J. Pharm. Pharmacol.* 36, p. 465-466, 1984) represent the most versatile approaches to coupling. Avidin-coupled and avidin and biotinyl-coupled phospholid liposomes containing actinomycin D have successfully targeted tumor cells expressing ganglio-N-triosylceramide (Urdal et al., *J. Biol. Chem.*, 255, p. 10509-10516, 1980). Huang et al. (*Biochim. Biophys. Acta*, 716, p. 140-150, 1982) demonstrate the binding of mouse monoclonal antibody to the major histocompatibility antigen H-2 (K), or goat antibody to the major glycoprotein of Molony Leukemia Virus, to palmitic acid. These fatty acid modified IgGs were incorporated into liposomes, and the binding of these liposomes to cells expressing the proper antigens characterized. Other in vitro efforts to specific binding of liposomes coated with specific immunoglobins have been performed (Sharkey et al., Fed. Proc., 38, p. 1089, 1979). In still other coupling studies, Rahman et. al. found that tissue uptake of liposomes could be altered by attachment of glycolipids to the liposomes (*J. Cell Biol.*, 83, p. 268a, 1979).

One aspect of the present invention is to couple biotinylated proteins such as immunoglobulins and antibodies to liposomes with covalently-attached streptavidin. Methods for this coupling are herein provided. The nature of this covalent attachment between streptavidin and the liposomes is a chemical bonding between the streptavidin, and derivatized phosphatidylethanolamine incorporated in the liposome bilayer. In a second aspect of the invention, Applicants provide a two-step method for the non-covalent coupling of these biotinylated proteins to biotinylated-phosphatidylethanolamine (PE)-containing liposomes through the same streptavidin linker. This non-covalent attachment of streptavidin and liposomes occurs through a specific association between four specific biotin binding sites on streptavidin, and the biotin. These antibody-liposome complexes bind specifically to target cells as directed by the coupled antibody. Such liposomes may be made to contain bioactive agents such as drugs.

In accordance with a primary use for liposomes, the entrapment of antineoplastic agents inside liposomal bilayers has resulted in more efficacious therapy as compared to direct administration of the drug. (Forsben et al., *Cancer Res.*, 43, p. 546, 1983; and Gabizon et al., *Cancer Res.*, 42, p. 4734, 1982). A problem with the encapsulation of antineoplastic drugs is in the fact that many of these drugs have been found to be rapidly released from liposomes after encapsulation. This is an especially undesirable effect, in view of the fact that toxicity of these agents can be significantly reduced through liposome encapsulation as compared to direct administration. See, for example, Forssen et al. *Cancer Res.* 43, 546 (1983) and Rahman et al. *Cancer Res.*, 42, 1817 (1982). Clearly, a method whereby drug could be loaded into preformed liposomes would be advantageous. To achieve this object, the invention, in accordance with one of its aspects, provides a method for loading liposomes with ionizable antineoplastic agents wherein a transmembrane potential is created across the walls of the liposomes and the antineoplastic agent is loaded into the liposomes by means of the transmembrane potential. See also U.S. patent application Ser. No. 749,161, Bally et al. entitled "Encapsulation of Antineoplastic Agents in Liposomes", filed June 26, 1985, relevant portions of which are incorporated herein by reference.

In accordance with these needs, a liposome composition is presented which describes the use of protein-coupled liposomes which may be stored stably for an indefinite period, in a dehydrated state, with loading of the liposomes on an "as needed" basis.

SUMMARY OF THE INVENTION

We have prepared a liposome composition whereby the glycoprotein streptavidin is coupled to liposomes for purposes of liposome targeting. The streptavidin may in turn couple biotinated proteins such as Immunoglobulin G or monoclonal antibodies and be loaded with a variety of bioactive agents, depending on use. Such agents may be the antineoplastic agents such as daunorubicin, doxorubicin, and vinblastine.

The liposomes are preferably prepared in such a way as to create a transmembrane potential across their lamellae in response to a concentration gradient. This concentration gradient may be created by either $Na^+/K^+$ potential or pH ($H^+$). The difference in internal versus external potential is the mechanism which drives the loading of the liposomes with ionizable bioactive agents; delayed loading of preformed liposomes will occur in response to the transmembrane potential. These liposomes may be dehydrated in the presence of one or more protecting sugars such as the disaccharides trehalose and sucrose, stored in their dehydrated condition, and subsequently rehydrated with retention of the ion gradient and associated ability to accumulate the bioactive agent. Such bioactive agents may be those used as in vivo pharmaceutical preparations, such as antineoplastic agents including doxorubicin. These preparations may be administered to a subject for treatment of disease. Alternatively, the coupled liposome preparations may be used in diagnostic assays. Methods are provided for the preparation of liposomes either covalently or non-covalently coupled to streptavidin, which in turn are complexed with biotinylated proteins such as IgG or monoclonal antibodies. In the case of non-covalent binding of liposomes to streptavidin, the liposomes comprise biotinylated Phosphatidylethanolamine. Such liposomes are incubated with, for example, about 10-fold molar excess streptavidin to biotinylated phosphatidylethanolamine (PE), to complete the coupling reaction. The liposomes may be large unilamellar vesicles, and may also comprise egg Phosphatidylcholine (EPC).

In preparations containing EPC and biotinylated PE, the latter is in an about 0.1 to 0.5% mole ratio with the EPC, preferably an about 0.1% mole ratio.

Compositions of protein-streptavidin-biotinylated PE liposomes wherein the protein is a monoclonal antibody or Immunoglobulin G are claimed. These liposomes may also comprise a bioactive agent. They may be used in vivo as a pharmaceutical preparation in a subject or alternatively in in vitro diagnostic assays by contacting a sample with the composition.

DETAILED DESCRIPTION OF THE INVENTION

Figure 1:
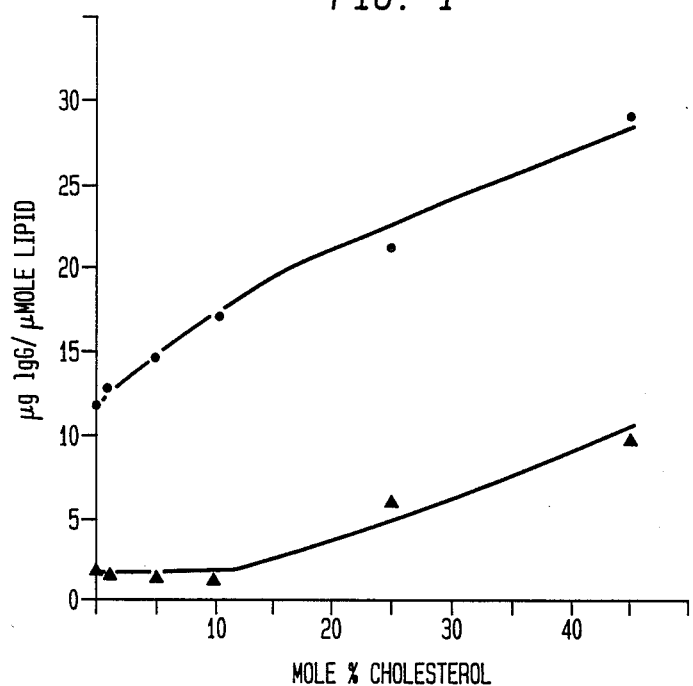
FIG. 1 is a graph showing coupling of anti-rat erythrocyte IgG to EPC LUVETs (labeled with $^3H$-DPPC) containing PDP-PE (closed triangle) and MPB-PE (closed circle) as a function of cholesterol content.

As described above, the present invention describes a liposome composition that results from the coupling of the liposomes to streptavidin. In addition, the composition can be dehydrated and rehydrated. The liposome portions can be loaded with a chosen bioactive agent by potential difference of ions across the bilayer membranes during the rehydration step or subsequently thereto. Alternatively, the bioactive agent may be added to the liposomes prior to dehydration. The streptavidin-coupled liposomes can be coupled to proteins such as Immunoglobulin G or monoclonal antibodies which have been biotinated by coupling to biotin. Quite surprising is the observed stability of the streptavidin-liposome-biotinated protein complex which makes streptavidin an attractive coupler between the liposomes and the targeting proteins. The proteins bound to the liposomes aid in targeting the liposomes and their contents to a specific site in the body.

In one embodiment of the present invention, liposomes are formed using the LUVET apparatus described in copending U.S. patent application entitled "Extrusion Technique for Producing Unilamellar Vesicles", Ser. No. 622,690, filed June 20, 1984, relevant portions of which are incorporated herein by reference, and covalently coupled to streptavidin using a modified technique of Leserman et al., (*Liposome Technology, III,* 1984, CRC Press, Inc., N.Y., p. 29–40). Liposomes are formed with a transmembrane potential i.e. $Na^+/K^+$ gradient or $H^+$ potential difference across the bilayers, see copending U.S. patent application, Ser. No. 749,161, Bally et al., entitled "Encapsulation of Antineoplastic Agents in Liposomes", filed June 26, 1985, relevant portions of which are incorporated herein by reference; this potential difference effected by the ionic concentrations of the internal versus the external media of the liposome. Liposomes are then dehydrated either in the presence or absence of sugars such as trehalose, and may be stored in this state for indefinite periods of time; see copending U.S. patent application, Ser. No. 759,419, Janoff et al., entitled "Dehydrated Liposomes," filed July 26, 1985, relevant portions of which are incorporated herein by reference.

In another embodiment of the present invention, biotinylated proteins are non-covalently coupled to biotinylated PE-containing liposomes via streptavidin. The non-covalent binding of the streptavidin to the liposomes, the first step, involves incorporation of biotin-PE in the liposomes, followed by a second step of binding the streptavidin to the biotinylated protein. The proteins are prepared for this binding by the use of fluorescent derivatizing reagents such as the fluorescent amine reagent fluorescein-isothiocyanate (FITC).

There are four biotin binding sites on the streptavidin, which makes liposomes containing biotin aggregate with streptavidin in an excess of biotinylated PE. Thus, the amount of biotinylated PE to incorporate into the liposomes was titrated in order to prevent this aggregation, while maximizing the streptavidin coupling. Values for biotinylated PE may range from about 0.05 to 0.5 mole % (with respect to total lipid in the liposome preparation); if the amount of biotin is increased further than about 0.5%, complete aggregation and precipitation of liposomes is observed on addition of streptavidin. This aggregation phenomenon may be exploited in the use of these systems in an aggregation-type diagnostic assay.

The biotinylated antibody is then attached to the streptavidin coated liposome. These liposomes effectively targeted specifically to their target cells with little non-specific binding.

The liposomes used in the present invention can have a variety of compositions and internal contents, and can be in the form of multilamellar, unilamellar, or other types of liposomes, or more generally, lipid-containing particles, now known or later developed. For example, the lipid-containing particles can be in the form of steroidal liposomes, Ser. No. 599,691, now abandoned, alpha-tocopherol containing liposomes, Ser. No. 786,740, now abandoned, stable plurilamellar liposomes (SPLVs), U.S. Pat. No. 4,522,803, issued June 11, 1985, monophasic vesicles (MPVs), U.S. Pat. No. 4,588,578, issued May 13, 1986, or lipid matrix carriers (LMC), U.S. Pat. No. 4,610,868, issued Sept. 9, 1986, the pertinent portions of which are incorporated herein by reference. Within the class of liposomes that may be used in the present invention is a preferred subclass of liposomes characterized in having solute distribution substantially equal to the solute distribution environment in which prepared. This subclass may be defined as stable plurilamellar vesicles (SPLV), monophasic vesicles (MPVs), and frozen and thawed multilamellar vesicles (FATMLVs) as described in "Solute Distributions and Trapping Efficiencies Observed in Freeze-Thawed Multilamellar Vesicles" Mayer et al. *Biochimica et Biophysica Acta* 817:1983–196 (1985). It is believed that the particular stability of the SPLV type liposomes arises from the low energy state attendant to solute equilibrium.

Alternatively, techniques used for producing large unilamellar liposomes (LUVs), such as, reverse-phase evaporation, infusion procedures, and detergent dilution, can be used to produce the liposomes. A review of these and other methods for producing liposomes can be found in the text *Liposomes*, Marc J. Ostro, ed., Marcel Dekker, Inc., New York, 1983, Chapter 1, the pertinent portions of which are incorporated herein by reference.

Compounds which are bioactive agents can be entrapped within the liposomes of the present invention. Such compounds include but are not limited to antibacterial compounds such as gentamycin, antiviral agents such as rifampacin, antifungal compounds such as amphotericin B, anti-parasitic compounds such as antimony derivatives, tumoricidal compounds such as adriamycin, anti-metabolites, peptides, proteins such as albumin, toxins such as diptheriatoxin, enzymes such as catalase, polypeptides such as cyclosporin A, hormones such as estrogen, hormone antagonists, neurotransmitters such as acetylcholine, neurotransmitter antagonists, glycoproteins such as hyaluronic acid, lipoproteins such as alpha-lipoprotein, immunoglobulins such as IgG, immunomodulators such as interferon or interleuken, vasodilators, dyes such as Arsenazo III, radiolabels such as $^{14}C$, radio-opaque compounds such as $^{90}Te$, fluorescent compounds such as carboxy fluorscein, receptor binding molecules such as estrogen receptor protein, anti-inflammatories such as indomethacin, antiglaucoma agents such as pilocarpine, mydriatic compounds, local anesthetics such as lidocaine, narcotics such as codeine, vitamins such as alpha-tocopherol, nucleic acids such as thymine, polynucleotides such as RNA polymers, psychoactive or anxiolytic agents such as diazepam, mono- di- and polysaccharides, etc. A few of the many specific compounds that can be entrapped are pilocarpine, a polypeptide growth hormone such as human growth hormone, bovin growth hormone and porcine growth hormone, indomethacin, diazepam, alpha-tocopherol itself and tylosin. Antifungal compounds include miconazole, terconazole, econazole, isoconazole, tioconazole, bifonazole, clotrimazole, ketoconazole, butaconazole, itraconazole, oxiconazole, fenticonazole, nystatin, naftifine, amphotericin B, zinoconazole and ciclopirox olamine, preferably miconazole or terconazole, The entrapment of two or more compounds simultaneously may be especially desirable where such compounds produce complementary or synergistic effects. The amounts of drugs administered in liposomes will generally be the same as with the free drug; however, the frequency of dosing may be reduced.

The liposomes of the present invention are preferably dehydrated using standard freeze-drying equipment or equivalent apparatus, and, if desired, the liposomes and their surrounding medium can be frozen in liquid nitrogen before being dehydrated. Alternatively, the liposomes can also be dehydrated without prior freezing, by simply being placed under reduced pressure. Dehydration with prior freezing requires the presence of one or more protective sugars in the preparation. A variety of sugars can be used, including such sugars as trehalose, maltose, sucrose, glucose, lactose, and dextran. In general, disaccharide sugars have been found to work better than monsaccharide sugars, with the disaccharide sugars trehalose and sucrose being most effective.

The one or more sugars are included as part of either the internal or external media of the liposomes. Most preferably, the sugars are included in both the internal and external media so that they can interact with both the inside and outside surfaces of the liposomes' membranes. Inclusion in the internal medium is accomplished by adding the sugar or sugars to the solute which the liposomes are to encapsulate. Since in most cases this solute also forms the bathing medium for the finished liposomes, inclusion of the sugars in the solute also makes them part of the external medium. Of course, if an external medium other than the original solute is used, e.g., to create a transmembrane potential (see below), the new external medium should also include one or more of the protective sugars.

In the case of dehydration without prior freezing, if the liposomes being dehydrated have multiple lipid layers and if the dehydration is carried out to an end point where there is sufficient water left in the preparation so that a substantial portion of the membranes retain their integrity upon rehydration, the use of one or more protective sugars may be omitted. It has been found preferable if the preparation contains at the end of the dehydration process at least about 2%, and most preferably between about 2% and about 5%, of the original water present in the preparation prior to dehydration.

Once the liposomes have been dehydrated, they can be stored for extended periods of time until they are to be used. When the dehydrated liposomes are to be used, rehydration is accomplished by simply adding an aqueous solution, e.g., distilled water, to the liposomes and allowing them to rehydrate.

As discussed above, in accordance with another of its aspects, the present invention provides a method for loading liposomes with ionizable antineoplastic agents wherein a transmembrane potential is created across the bilayers of the liposomes and the antineoplastic agent is loaded into the liposomes by means of the transmembrane potential. The transmembrane potential is generated by creating a concentration gradient for one or more charged species (e.g., $Na^+$, $K^+$ and/or $H^+$) across the liposome membranes. The concentration gradient is created by producing liposomes having different internal and external media, i.e., internal and external media having different concentrations of one or more charged species.

Specifically, liposomes are prepared which encapsulate a first medium having a first concentration of the one or more charged species. For a typical liposome preparation technique (see discussion above), this first medium will surround the liposomes as they are formed, and thus the liposomes' original external medium will have the same composition as the first medium. To create the concentration gradient, the original external medium is replaced by a new external medium having a different concentration of the one or more charged species. The replacement of the external medium can be accomplished by various techniques, such as, by passing the liposome preparation through a gel filtration column, e.g., a Sephadex column, which has been equilibrated with the new medium, or by centrifugation, dialysis, or related techniques.

In accordance with the invention, it has been found that this transmembrane potential can be used to load ionizable antineoplastic agents into the liposomes. Specifically, once liposomes having a concentration gradient and thus a transmembrane potential of the appropriate orientation have been prepared, the process of loading antineoplastic agents into the liposomes reduces to the step of adding the agent to the external medium. Once added, the transmembrane potential will automatically load the agent into the liposomes.

The transmembrane potential loading method can be used with essentially any antineoplastic agent which can exist in a charged state when dissolved in an appropriate aqueous medium (e.g., organic compounds which include an amino group which can be protonated). Preferably, the agent should be relatively lipophilic so that it will partition into the liposome membranes. Examples of some of the antineoplastic agents which can be loaded into liposomes by this method include doxorubicin, mitomycin, daunorubicin, streptozocin, vinblastine, vincristine, mechlorethamine hydrochloride, melphalan, cyclophosphamide, triethylenethiophosphoramide, carmustine, lomustine, semustine, hydroxyurea, thioguanine, decarbazine, cisplatin, procarbazine, and pharmaceutically acceptable salts and derivatives thereof.

In addition to loading a single antineoplastic agent, the method can be used to load multiple antineoplastic agents, either simultaneously or sequentially. Also, the liposomes into which the ionizable antineoplastic agents are loaded can themselves be pre-loaded with other antineoplastic agents or other drugs using conventional encapsulation techniques (e.g., by incorporating the drug in the buffer from which the liposomes are made).

Turning now to the aspects of the invention relating to reducing the rate of release of an ionizable antineoplastic agent or other ionizable biologically-active agent (drug) from liposomes, it has been surprisingly found that the rate of release can be markedly reduced by creating a transmembrane potential across the liposome membranes which is oriented to retain the agent in the liposomes. That is, for an agent which is positively charged when ionized, a transmembrane potential is created across the liposome membranes which has an inside potential which is negative relative to the outside potential, while for an agent which is negatively charged, the opposite orientation is used.

As with the transmembrane loading aspects of the invention, the transmembrane potentials used to reduce the rate of drug release are created by adjusting the concentrations on the inside and outside of the liposomes of a charged species such as $Na^+$, $K^+$ and/or $H^+$. Indeed, if the liposomes have been loaded by means of a transmembrane potential produced by such a concentration gradient, simply keeping the liposomes in an external medium which will maintain the original concentration gradient will produce the desired reduction in the rate of release. Alternatively, if a transmembrane potential has not already been created across the liposome membranes, e.g., if the liposomes have been loaded using a conventional technique, the desired transmembrane potential can be readily created by changing the composition of the external medium using the exchange techniques described above.

Turning next to the aspects of the invention relating to the dehydration protocols, two basic approaches are provided: (1) the liposomes can be loaded with antineoplastic agents (e.g., using conventional techniques or the transmembrane potential loading technique described above), dehydrated for purposes of storage, shipping, and the like, and then rehydrated at the time of use; or (2) pre-formed liposomes can be dehydrated for storage, etc., and then at or near the time of use, they can be rehydrated and loaded with an ionizable antineoplastic agent using the transmembrane potential loading technique described above.

When the dehydrated liposomes are to be used, rehydration is accomplished by simply adding an aqueous solution, e.g., distilled water or an appropriate buffer, to the liposomes and allowing them to rehydrate. The liposomes can be resuspended into the aqueous solution by gentle swirling of the solution. The rehydration can be performed at room temperature or at other temperatures appropriate to the composition of the liposomes and their internal contents.

If the antineoplastic agent which is to be administered was incorporated into the liposomes prior to dehydration, and no further composition changes are desired, the rehydrated liposomes can be used directly in the cancer therapy following known procedures for administering liposome encapsulated drugs.

Alternatively, using the transmembrane potential procedures described above, ionizable antineoplastic agents can be incorporated into the rehydrated liposomes just prior to administration. In connection with this approach, the concentration gradient used to generate the transmembrane potential can be created either before dehydration or after rehydration using the external medium exchange techniques described above.

For example,, liposomes having the same internal and external media, i.e., no transmembrane potentials, can be prepared, dehydrated, stored, rehydrated, and then the external medium can be replaced with a new medium having a composition which will generate transmembrane potentials, and the transmembrane potentials used to load ionizable antineoplastic agents into the liposomes. Alternatively, liposomes having internal and external media which will produce transmembrane potentials can be prepared, dehydrated, stored, rehydrated, and then loaded using the transmembrane potentials.

Liposomes of the present invention may be administered to a subject such as a mammal including humans. For administration to humans in the treatment of afflictions, the prescribing physician will ultimately determine the appropriate dose for a given human subject, and this can be expected to vary according to the age, weight, and response of the individual as well as the nature and severity of the patient's symptoms.

The mode of administration may determine the sites and cells in the organism to which the compound will be delivered. For instance, delivery to a specific site of infection may be most easily accomplished by topical application (if the infection is external e.g., on areas such as eyes, skin, in ears, or on afflictions such as wounds or burns) or by absorption through epithelial or mucocutaneous linings (e.g., nasal, oral, vaginal, rectal, gastrointestinal, mucosa, etc.). Such topical application may be in the form of creams or ointments. The liposome-entrapped materials can be administered alone but will generally be administered in admixture with a pharmaceutical carrier selected with regard to the intended route of administration and standard pharmaceutical practice. They may be injected parenterally, for example, intravenously, intramuscularly, or subcutaneously. For parenteral administration, they are best used in the form of a sterile aqueous solution which may contain other solutes, for example, enough salts or glucose to make the solution isotonic.

For the oral mode of administration, liposome composition of this invention can be used in the form of tablets, capsules, lozenges, troches, powders, syrups, elixirs, aqueous solutions and suspensions, and the like. In the case of tablets, carriers which can be used include lactose, sodium citrate, and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, certain sweetening and/or flavoring agents can be added.

The liposomes of this invention may also be used in diagnostic assays; in this case the amount of the composition used will depend on the sensitivity of the liposome-coupled antibody to the target components in the sample.

MATERIALS AND METHODS

Egg phospatidylcholine (EPC) was isolated from hen egg yolk employing established procedures. Egg phosphatidylethanolamine (EPE) was obtained from EPC utilizing the headgroup exchange capacity of phospholipase D (Kates et al., *Methods in Enzymology*, 14, Lavenstein, J. ed., 1969, Academic Press, Inc., p. 197–211). Dioleoylphosphatidylcholine (DOPC) and dipalmitoylphosphatidylcholine (DPPC) were obtained from Avanti Polar Lipids. Strepavidin, cholesterol, trehalose, dithiothreitol (DTT), and fluorescein isothiocyanate Celite (Celite FITC) were purchased from Sigma. N-Succinimidyl 3-(2-pyridyldithio) propionate (SPDP), N-succinimidyl 4-(p-Maleimidophenyl)butyrate (SMPB), biotinyl-N-hydroxysuccinimide (BHS) biotin-phosphatidylethanolasine, and N-biotinoyldipalmitoylphosphatidylcholine were obtained from Molecular Probes. Rabbit anti-human red blood cell IgG and Rabbit anti-rat red blood cell IgG were supplied by Cooper Biomedical. Sephadex G-50 fine, Sepharose 4B-CL, and Sepharose C14B were purchased from Pharmacia. [$^3$H]-DPPC and [$^3$H]-BHS were obtained from NEN, carrier free Na $^{125}$I (100 mCi/ml) was supplied by Amersham and iodogen was obtained from Pierce. Adriamycin was obtained from B.C. Cancer Control Agency. Biotinylated anti-rat erythrocyte IgG was obtained from Cappel. All other chemicals were of analytical grade.

Lipid was estimated by the standard lipid phosphate assay or by incorporation of trace quantities of [$^3$H-DPPC] introduced in the original lipid film, and later monitored using a Packard Tri-Carb 4000 series scintillation counter. FITC was assayed by monitoring the fluorescence at 520 nm using a SLM-Aminco SPF-500C spectrofluotometer with an excitation wavelength of 495 nm. $^{125}$I was measured using a Packard Auto-Gamma 5650 gamma counter. Vesicle size distributions were determined by quasi-elastic light scattering (QELS) analysis utilizing a Nicomp Model 270 submicron particle sizer operating at 632.8 nm and 5 mW.

EXAMPLE 1

Covalent Coupling

I. Synthesis of N-[4-(p-Maleimidophenyl)butyryl] phosphatidylethanolamine (MPB-PE)

MPB-PE was prepared according to the procedure of Martin et al., *J. Biol. Chem.*, 257, 286–288, (1982). EPE (200 mg) was dissolved in 5 ml of freshly distilled anhydrous methanol containing 200 umol of freshly distilled triethylamine and 100 mg SMBP. The reaction was carried out at room temperature under nitrogen and its progress followed using thin layer chromatography (TLC, running solvent:chloroform/methanol/water, 65:25:4). Following an 18 hour incubation, 95% of the EPE was converted to MPB-PE. Methanol was removed under reduced pressure and redissolved in chloroform and this mixture washed extensively with 1% NaCl to remove unreacted SMPB and residual triethylamine. The product of this reaction was characterized by two dimensional TLC and proton NMR. This analysis indicated the presence of two components, one being MPB-PE and comprising approximately 60% of the product. The product of the reaction mixture described above was incorporated into vesicles without additional Purification. The product was stored at −20° C. and was shown to be stable for at least 6 months.

II. Synthesis of N-[3(2-Pyridyldithio)Proprionyl] phosphatidylethanolamine (PDP-PE)

PDP-PE was prepared according to the procedure of Leserman et al., *Liposome Technology, III.* Gregoriadis, ed., 1984, CRC Press, Inc., CA., p. 29–40. Briefly, 50 umol EPE was dissolved in 3.5 ml chloroform/methanol (9:1) and added to 1.5 ml methanol containing 60 umol SPDP and 100 umol triethylamine. After a four hour incubation at room temperature, TLC (solvent: chloroform/methanol/water, 65:25:4) analysis indicated 99% conversion of EPE to a faster running product. This reaction mixture was washed with 10 ml of phosphate buffered saline (0.1M NaCl, 0.1M potassium phosphate, pH 7.4). This was repeated three additional times prior to removal of the organic phase under reduced pressure. Further analysis by two dimensional TLC and proton NMR indicated a single product which appeared greater than 98% pure. PDP-PE was stored under $N_2$ in chloroform at −20° C. and was stable for at least six months.

III. Vesicle Preparation

Large unilamellar vesicles (LUVs) were prepared employing the LUVET (LUV's by extrusion techniques) procedure described by Hope et al., *Biochim, Biophys. Acta,* 812, p. 55–65 (1985). Appropriate mixtures of lipid were deposited as a dry lipid film by evaporation from chloroform under a stream of nitrogen gas, placed under vacuum for at least two hours and subsequently hydrated with appropriate buffer by vortex mixing to produce multilamellar vesicles (MLVs). Frozen and thawed MLV (FATMLV) systems as described in Mayer et.al, *Biochim. et Biophys. Acta,* 817, 193–196 (1985), were obtained by freezing the MLV's in liquid nitrogen and thawing at 40° C., a cycle which was repeated five times. These FATMLV's were then extruded under nitrogen pressure ten times through two stacked Nucleopore polycarbonate filters of defined pore size. Generally a pore size of 100 nm was employed resulting in a preparation of unilamellar vesicles (VET$_{100}$) with an average diameter of 110 nm as determined by QELS measurements. Vesicles of variable sizes were produced by similar extrusion techniques through filters with pore sizes ranging from 30 nm to 400 nm. Unless specified differently vesicles were prepared in a NaCl/EPPS buffer (150 mM NaCl, 20 mM EPPS, (N-2-Hydroxyethylpiperazinepropanesulphonic acid) pH 8.0) at a final lipid concentration of 10 umol/ml. In vesicles which contained PDP-PE, the presence of this lipid was verified by measuring the release of 2-thiopyridinone upon addition of DTT (25 mM final concentration) as indicated previously.

IV. Preparation of Proteins Used for Coupling

IgGs and streptavidin were modified with the amine reactive heterobifunctional reagent SPDP according to Leserman et al. (supra.). Biotin-conjugated antibodies were prepared according to Bayer et al., *Biochim et Biophys Acta,* 550, p. 464–473, (1979).

V. Covalent Coupling of Proteins to Vesicles

The steps utilized to crosslink proteins to liposomes are as follows: thio-reactive lipids were generated, PDP-PE and MPB-PE, according to the procedures of Leserman, et al., supra., and Martin et al., supra., respectively. These derivatized PE's were incorporated into vesicles, at levels of 5 mol % based on total modified lipid content. Since the MPB-PE was shown to be less than 60% pure by two dimensional TLC and $^1$H-NMR, the vesicles prepared with "MPB-PE" actually contained only 3% of this modified lipid. Thus, for vesicles prepared as described above, 100 ul of vesicles were added to 100 to 500 ul of the protein solution depending on protein concentration. This reaction mixture (pH=8.0) was incubated in the dark under nitrogen for 12 to 18 hours unless specified differently. Subsequently the liposomes were separated from unassociated protein employing a Sepharose 4B-CL column (column volume equivalent to a least 20 times the sample volume) equilibrated with NaCl/Hepes buffer. Protein and total lipid concentrations in the fractions were determined directly or calculated from the specific activities of $^{125}$I-labeled protein and [$^3$H]-DPPC, respectively. Where FITC-labeled proteins were used fractions were dissolved in ethanol to a total volume of 2 ml and the fluorescence was determined and compared to the fluorescence associated with a known quantity of fluoresceinated protein. The presence of lipid was shown not to influence fluorescence in this assay system.

Binding of biotinated-IgGs to avidin-coupled vesicles was assessed as described above after a 30 minute incubation at room temperature. IgG was generally added at equimolar concentrations with respect to avidin present in the incubation mixture.

Protein modification with the heterobifunctional reagent SPDP was shown to be extremely reproducible provided the DPDP was freshly prepared and stored anhydrously. This reaction resulted in the substitution for IgG in the range of 4 to 5 moles 2-dithiopryidinone (2-DT) per mole IgG (regardless of the IgG used) and for protein A and streptavidin 6 to 7 moles 2-DT per mole protein based on an incubation ratio of 10 moles SPDP per mole protein. It was demonstrated that this extent of modification did not influence the binding activity of a monoclonal IgG (anti-transferring receptor IgG) or the ability of streptavidin to bind biotin.

The reaction mixture used for coupling consisted of vesicles containing one of the thio-reactive lipids plus the modified protein bearing several thiol groups, as judged by the release of 2-DT on addition of DTT. Following an incubation period of 18 hours, the vesicles and associated protein were fractionated from free protein on Sepharose 4B-CL columns and the lipid and protein were quantified as indicated in the methods.

Martin et al. (*Ann. N.Y. Acad. Sci.,* 446, p. 443–456, 1985) had suggested that the thio-reactive PE derivatives function better in the presence of cholesterol. The amount of IgG coupling obtained with vesicles prepared with PDP-PE or MPB-PE was compared as a function of cholesterol content. The results, shown in FIG. 1, indicate that IgG crosslinking to vesicles containing PDP-PE does not occur unless the composition includes greater than 20 mol % cholesterol. Conversely, levels of 12 ug IgG per umole lipid were obtained for vesicles containing the SMPB derivative of PE even in the absence of cholesterol. This amount of association increased linearly with respect to the amount of cholesterol included in the vesicles to levels approaching 30 ug IgG per umole lipid for vesicles containing 45 mol % cholesterol.

Figure 2A:
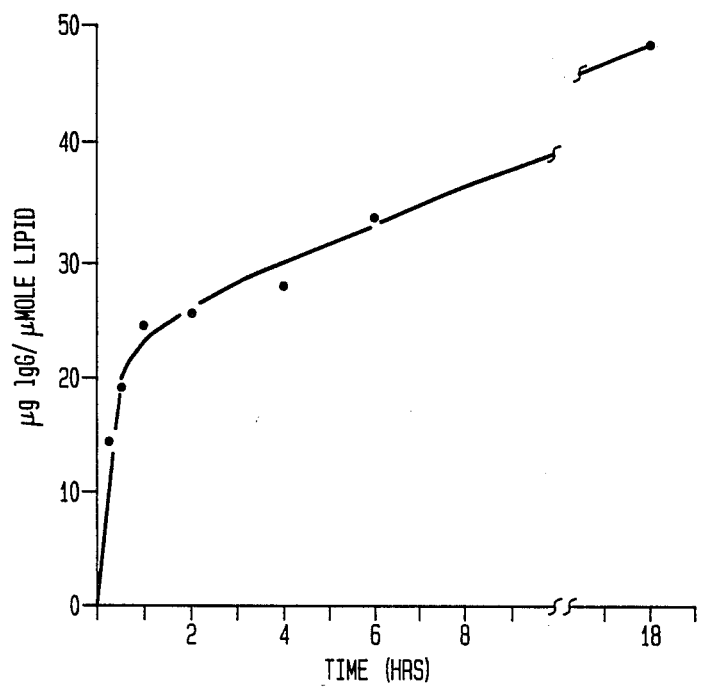
FIG. 2 is a graph characterizing the covalent coupling reaction of IgG to vesicles with regards to time course, of (A), MPB-PE concentration (B) and IgG concentration (C).
Figure 2B:
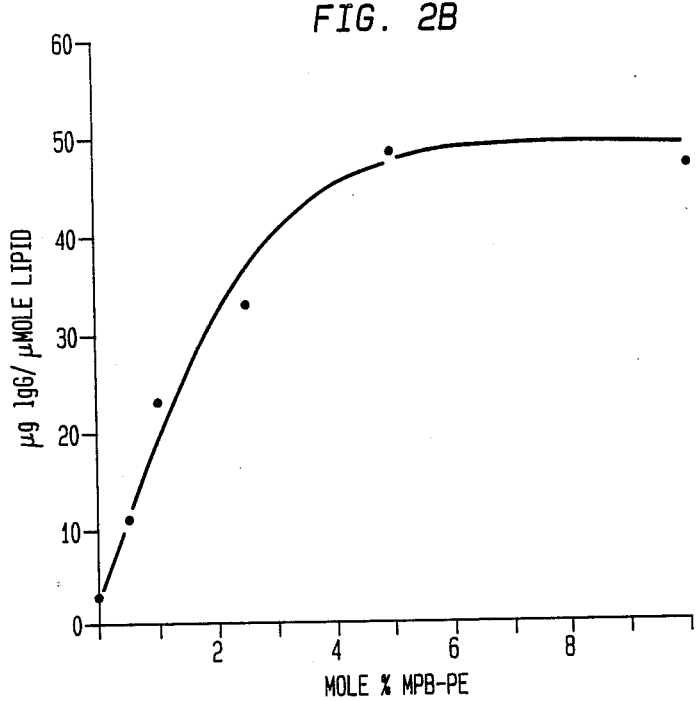
Figure 2C:
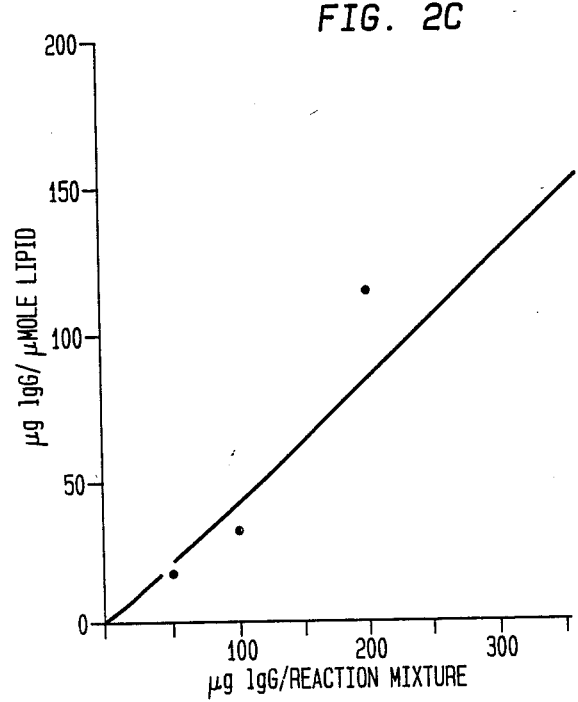

The reaction of SPDP modified proteins with MPB-PE was extensively characterized. The time course for coupling IgG (FIG. 2A) suggests that the reaction proceeds in two phases. Approximately 25 ug of IgG was coupled to vesicles within one hour. Subsequently, the rate of association decreased several fold, but continued linearly for at least 18 hours. As indicated in FIG. 2B, maximum coupling was obtained when the vesicles were prepared with 5 mol % MPB-PE. Similar levels of IgG coupling were obtained with 10 mol % MPB-PE, however there was a significant amount of vehicle crosslinking in this preparation as judged by an increases in the optical density of the reaction mixture and greater than 50% loss of both lipid and protein on the Sepharose 4B-CL gel filtration column. The amount of IgG coupling to vesicles increased linearly with increased amounts of modified IgG present in the incubation mixture (FIG. 2C). Assuming a vesicle diameter of 100 nm, levels of 170 ug IgG per umole lipid, also resulted in vesicle crosslinking.

Figure 3:
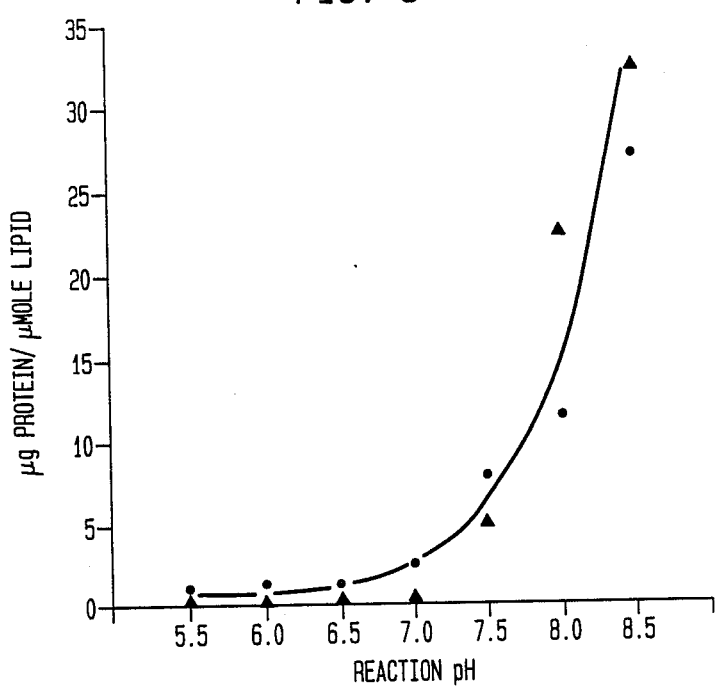
FIG. 3 is a graph showing the influence of reaction pH on covalent coupling of anti-human erythrocyte IgG (closed circle) and streptavidin (closed triangle) to EPC/Chol (50:45) vesicles containing 5 mol % MPB-PE.

The extent of protein coupling was shown to be dependent on the pH of the reaction mixture (FIG. 3). Contrary to previous work which performed similar coupling reactions at pH 6.7, (Heath et.al, *Proc. Natl. Acad. Sci U.S.A.*, 80, p. 1377-1381, (1983), Bragman et al., *Biochim. Biophys. Acta*, 730, p. 187-195, (1983), and Bragman et al., *JNCI*, 73, p. 127-131, (1984), modified IgG and streptavidin coupling to vesicles occurred only at pHs greater than 8.0. At pH values below 7.0, only background protein-lipid association was observed.

Figure 4:
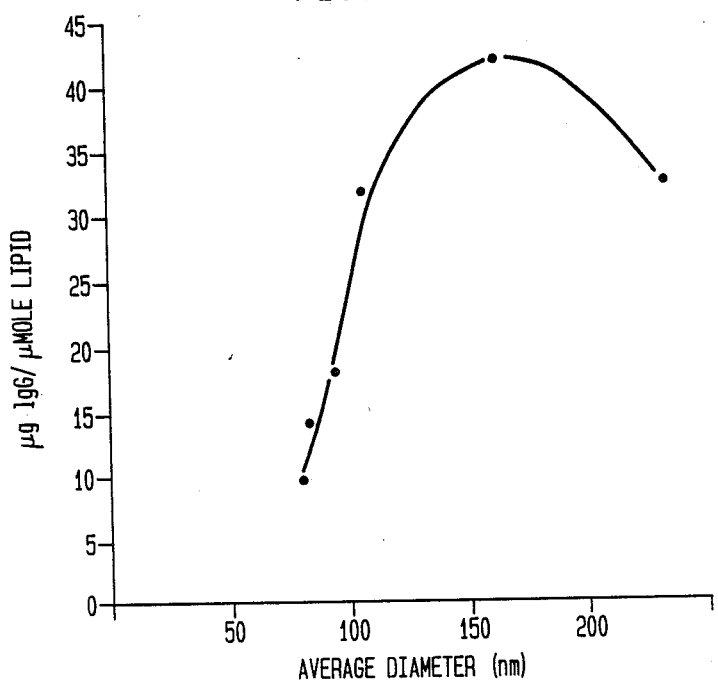
FIG. 4 is a graph showing the efficiency of covalent coupling of anti-human erythrocyte IgG to vesicles of variable size.

As shown in FIG. 4, the amount of IgG crosslinking was dependent on the size of the vesicle employed. The maximum efficiency of the coupling reaction never exceeded 45% based on the amount of protein present in the reaction mixture. However, for vesicles which had been sized through the 200 nm pore size filters, showing an average diameter of 162+/−41 nm by QELS measurements, the ratio of available MPB-PE to IgG approached 1 indicating that the maximum level of crosslinking was obtained. Based on the QELS approximated average diameters, 3950, 75, and 20 IgG molecules were bound to the 162 nm, 115 nm and 82 nm vesicles, respectively. Similar results have been obtained for sonicated vesicles when compared to vesicles produced by the reverse phase-evaporation technique and sized through 0.2 and 0.4 um pore size filters.

Finally, the influence of lipid composition on the coupling of proteins to vesicles containing MPB-PE was determined. The results shown in Table 1 emphasize previous results (FIG. 1), and demonstrate that IgG coupling to vesicles is much more efficient when cholesterol is incorporated. Crosslinking of the smaller streptavidin (68,000 daltons vs. 150,000 daltons for IgG) was not influenced by addition of this sterol. These data also indicate that incorporation of either a negative charge (phosphatidylserine or "PS") or a positive charge (stearylamine or "SA") into the liposome does not influence the extent of coupling for either protein.

VI. Binding of biotinated-IgG to stepavidin coupled vesicles ("Avisomes")

Figure 5:
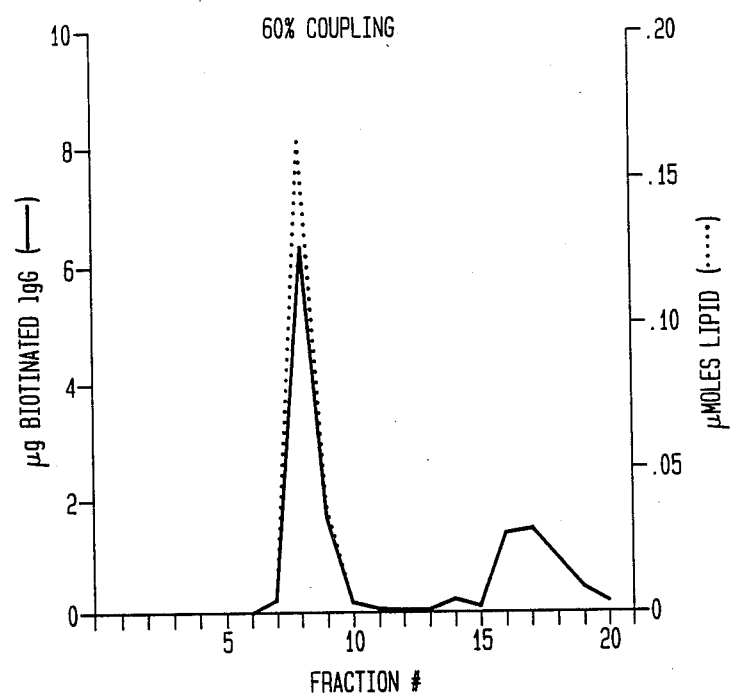
FIG. 5 is a graph showing the elution profile for biotinated anti-human erythrocyte IgG to vesicles which have covalently coupled streptavidin.

An advantage can be obtained if a single vesicle preparation is employed to couple a variety of different immunoglobulins. It has been shown that not all IgGs can be modified with the reagent SPDP such that they retain binding activity (Heath et.al, supra), and that certain IgGs which have been extensively modified with SPDP could not be crosslinked efficiently by the procedures described above. Leserman et. al, supra., recognized these limitations and circumvented them somewhat by coupling protein A to liposomes. Since protein A binds the Fc portion of IgGs of certain subclass (IgG2a), protein A coupled vesicles specifically bound to cells preincubated with a variety of antibodies. This allowed for a comparison of a number of different parameters using a single vesicle preparation. A similar yet more general approach can be achieved by taking advantage of the strong affinity ($Kd=10^{-15}M$) of biotin for streptavidin. Since IgGs can be easily biotinated, Bayer et al., supra; and Heitzmann et al. *Proc. Natl. Acad. Sci. U.S.A.*, 71, p. 3537-3541, (1974), a streptavidin coupled vesicle can be used to bind any number of IgGs with differing specificities. This application of "Avisomes" is illustrated in FIG. 5, which shows the elution profile for "avisomes") following a thirty minute incubation with biotinated-IgG (4 biotins per IgG). More than 40 ug IgG were bound per umole lipid which corresponded to approximately 100 IgGs per vesicle. Similar levels of association were obtained for three different IgG and could be obtained at biotin/IgG ratios of less than 2. In addition, the efficiency of this association was better than that observed for the chemical crosslinking procedures employed previously.

VII. Dehydration of protein-coupled vesicles and entrapment of adriamycin

Strepavidin-coupled vesicles ("avisomes") were dehydrated according to the procedure of Madden et al., *Biochim. Biophys Acta*, 817, p. 67-74, (1985). Vesicles were prepared as described above in a citrate buffer (100 mM citric acid, 150 mM KOH, pH 4.5) which contained 250 mM trehalose. Subsequently the external buffer was exchanged for NaCl/EPPS buffer, thereby establishing a transmembrane electrical potential which can be utilized for accumulating adriamycin. Following the previously described coupling reaction, unassociated protein was separated from vesicles as described above employing a Sepharose 4B-CL column equilibrated with NaCl/Hepes buffer containing 250 mM trehalose. Vesicles with bound protein were divided into 1 ml aliquots and dried in 10 ml Kimex tubes at room temperature under vacuum for 24 hours.

Following dehydration, samples were rehydrated by addition of 900 ul distilled water. The resulting preparation was characterized with respect to binding of several biotinated-IgG and the ability to accumulate adriamycin. Adriamycin was quantitated by determining the absorbance at 480 nm of a triton X-100 solubilized sample which has been fractionated on Sephadex G-50 to remove unassociated adriamycin.

Figure 6:
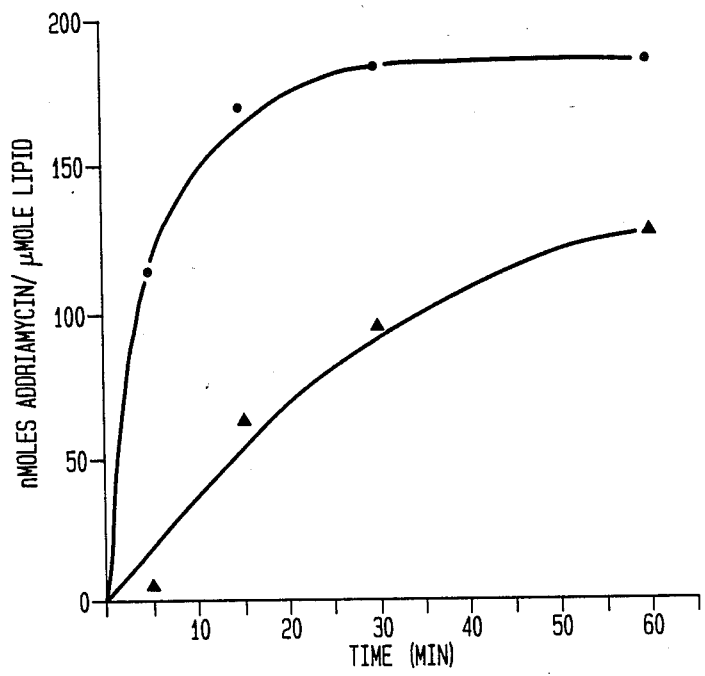
FIG. 6 is a graph showing the accumulation of adriamycin into covalently-coupled streptavidin-vesicles ("avisomes") which were prepared with a transmembrane pH gradient. Vesicles composed of EPC (closed circle) or EPC/Chol (closed triangle).

As shown in FIG. 6 "avisomes" can accumulate adriamycin in response to a preexisting pH gradient, where levels of 180 and 120 nmoles adriamycin per umole lipid are obtained for streptavidin coupled vesicles composed of EPC and EPC/Chol (1:1), respectively.

The ability to store "avisomes" in a dehydrated form was then demonstrated (Table 2). In these experiments vesicles were prepared in the presence of trehalose with removal of untrapped trehalose performed Prior to coupling, by gel filtration. Following the coupling reaction trehalose was added (final concentration =250 mM) to the streptavidin coupled vesicles and then dehydrated as described previously. There was little change in the amount of streptavidin bound to rehydrated "avisomes". Moreover, the biotin binding activity of streptavidin associated with vesicles (units per umole lipid) was not influenced by this dehydration step. This is also reflected in the ability of these preparations to bind biotinated-IgG to the same extent observed prior to dehydration.

EXAMPLE 2

Non-Covalent Coupling

Figure 7:
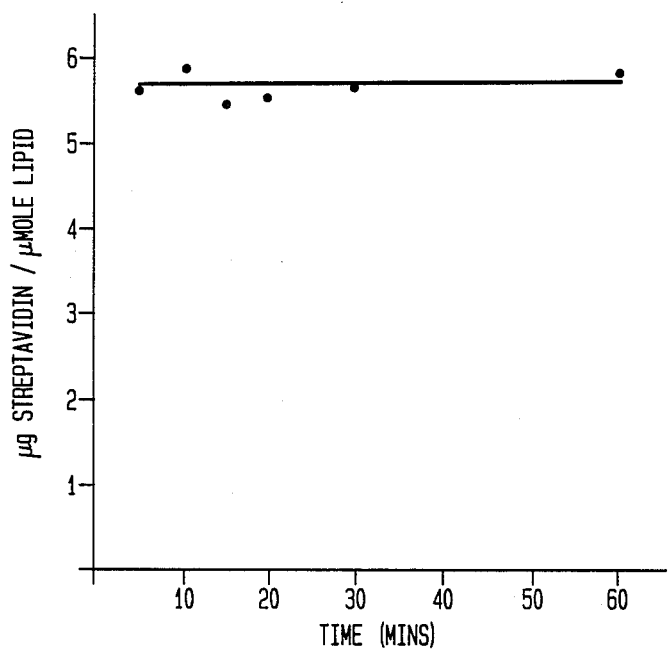
FIG. 7 is a graph showing the non-covalent coupling of streptavidin to LUVs containing biotinylated phosphatidylethanolamine.

Biotinylated PE was incorporated into egg phosphatidylcholine (EPC) at a molar ratio of 0.1% (with respect to PC) and LUVs produced by an extrusion procedure through 100 nm filters (Hope et al., supra.), and using a freeze and thaw technique (Bally et al., 1985, *Biochim. et Biophys. Acta.*, 812, 66–76), resulting in vesicles of approximately 100 nm diameter. The vesicles were incubated at 25° C. for 30 minutes at pH 8.0 in 10 fold molar excess of streptavidin (with respect to PE) in 20 mM EPPS buffered saline. At 5, 10, 15 and 20 minute intervals, aliquots were fractioned on Sepharose C14B columns (5 ml) to separate liposomally-bound streptavidin from free streptavidin (FIG. 7). The ratio of streptavidin bound per umole total lipid was determined to be at streptavidin:biotinylated PE ratios of 1:12 (mol/mol). This resulted in a maximum of 5.8 ug of streptavidin bound per umol lipid.

Biotinylated anti-rat erythrocyte IgG was prepared with 1–5 biotins covalently bound per mole of antibody by the method of Bayer et al., supra. FITC-labelling of biotinated antibodies was performed by incubation of antibody (5 mg/ml in PBC) with celite-FITC (2.5 mg/ml in 0.1 mM NaCl, 0.2M Na bicarbonate, pH 8.8) for 20 minutes at 25C, followed by gel filtration on Sepharose G50 (50 ml column). Antibody-streptavidin-liposomes were prepared by incubation of FITC-labelled biotin antibody (1 mg/ml) with streptavidin liposomes (1–2.5 umoles/ml) for 30 minutes at 25° C., at a 4-fold mole ratio of antibody to streptavidin. The final product was separated from free antibody by gel filtration on a Sepharose C14B column (15 ml). Phospholipid was assayed using the standard phosphate assay of Bartlett et al.)

EXAMPLE 3

Non-Covalent Coupling

The methods of Example 2 were followed using 0.05, 0.15, 0.25, 0.35, and 0.5 mole % biotinylated PE with EPC in the liposomes. This linearly increased the amount of streptavidin bound per liposome, by increasing the number of sites available for biotinylated antibody to couple to liposomes. A constant ratio of streptavidin was maintained with respect to total lipid.

EXAMPLE 4

Targeting of Non-Covalently Coupled Systems

Biotinylated anti-rat IgG or Biotinylated F(ab)2 fragments were coupled to LUVs as in Example 2. These LUVs contained 125I-labelled tyramine insulin (25 nmoles EPC, 25 nmoles biotin PE, 0.027 uCi 125I insulin/umol lipid), according to the procedures of Sommerman et al., 1984, *Biochim. et Biophys. Res Comm.*, 122, 319–324. The high specific activity of this entrapped marker allowed the in vitro distribution of the vesicle antibody complexes to be determined. For the preparation of biotinated F(ab)2 fragments, biotinated anti-rat erythrocyte IgG (4 biotins/IgG) was digested with pepsin in 0.1M Na acetate, pH 4.5 at 37° C. overnight (Nisoff et al., 1960, *Arch. Biochem. Biophys.*, 89, 230–244). The products were fractionated on a Sephadex G150 column and fractions containing F(ab)2 fragments, as determined by 10% SDS polyacrylamide gel (Laemmli, 1970, *Nature.* 227, 680–685) were pooled. F(ab)2 or antibody streptavidin liposomes were prepared as in Example 2. For erythrocyte cell binding studies, rat or human erythrocytes were washed with 20 mM EPPS buffered saline, pH 8, three times. Lipid (0.62 umol/ml) was incubated with $10^9$ erythrocytes in each experiment for 1 hour at 4° C., with the exception of (a) (see Table 1), where the lipid concentration was 1.76 umol/ml. Cells were washed three times with 20 mM EPPS buffered saline, PH 8, and were counted to determine levels of erythrocyte-associated liposomes.

As shown in Table 3, little non-specific binding of biotinylated liposomes to rat or human erythrocytes was observed. Anti-rat erythrocyte IgG or F(ab)2 liposome complexes bind specifically to rat erythrocytes but not to human erythrocytes.

TABLE 1
EFFECT OF LIPID COMPOSITION ON COUPLING

| Lipid Composition | ug IgG per umole Lipid | ug Streptavidin per umole Lipid |
|---|---|---|
| DPPC/CHOL | 41 | N.D. |
| DPPC | 8.2 | N.D. |
| DOPC/CHOL | 42 | 38.3 |
| DOPC | 20 | 36.0 |
| EPC/CHOL | 27 | 42 |
| EPC | 4.3 | 36 |

TABLE 2
STORAGE OF STREPAVIDIN COUPLED VESICLES

| Sample | ug Strepavidin per umole Lipid (ug from units) | Units per umole Lipid | Biotinated igG per umole Lipid |
|---|---|---|---|
| 24 Hrs in Buffer | 41 | N.D. | N.D. |
| 24 Hrs in Trehalose | 43(56) | 0.80 | 42.75 |
| Dehydrated with Trehalose | 50 (57) | 0.80 | 42.65 |

TABLE 3
Binding of targeted liposomes to rat erythrocytes

| | No. of liposomes bound per | |
|---|---|---|
| Sample | rat erythrocyte | human erythrocyte |
| Liposomes | 18 | ND |
| Streptavidin-liposomes | 20 | ND |
| (a)Pre-incubation with IgG + streptavidin-liposomes | 542 | ND |
| IgG streptavidin-liposomes | 416 | 11 |
| IgG streptavidin-liposomes + biotin | 73 | ND |
| F(ab)2 streptavidin liposomes | 302 | 11 |
| F(ab)2 streptavidin liposomes + biotin | 50 | ND |

ND = Not Done

We claim:
1. A streptavidin-coupled liposome.
2. The streptavidin-coupled liposome of claim 1 wherein the streptavidin is coupled to the liposome covalently.

3. The streptavidin-coupled liposome of claim 1 wherein the streptavidin is coupled to the liposome non-covalently.

4. The streptavidin-coupled liposome of claim 1 wherein the liposome contains a bioactive agent.

5. The streptavidin-coupled liposome of claim 1 wherein the liposome has a transmembrane potential.

6. The streptavidin-coupled liposome of claim 5 wherein the liposome contains a bioactive agent.

7. The streptavidin-coupled liposome of claim 1 wherein the composition is dehydrated.

8. The streptavidin-coupled liposome of claim 1 wherein the liposome contains a bioactive agent and has a transmembrane potential, and wherein the composition is dehydrated.

9. A pharmaceutical composition comprising the streptavidin-coupled liposome of claim 1 and a pharmaceutically acceptable carrier or diluent.

10. The streptavidin-coupled liposome of claim 1 wherein streptavidin is additionally coupled to a biotinated protein.

11. The streptavidin-coupled liposome of claim 10 wherein the protein is Immunoglobulin G.

12. The streptavidin-coupled liposome of claim 10 wherein the protein is a monoclonal antibody.

13. A method for preparing a liposome non-covalently coupled to streptavidin comprising the steps of:
 (a) preparing liposomes comprising biotinylated phosphatidylethanolamine; and
 (b) incubating the liposomes in streptavidin.

14. The method of claim 13 wherein the liposomes are large unilamellar vesicles.

15. The method of claim 13 wherein the liposomes also comprise egg phosphatidylcholine.

16. The method of claim 15 wherein the biotinylated phosphatidylethanolamine is in an about 0.1%–0.5% mole ratio with the egg phosphatidylcholine.

17. The method of claim 16 wherein the biotinylated phosphatidylethanolamine is in an about 0.1% mole ratio with the egg phosphatidylcholine.

18. The method of claim 13 wherein step (b) is performed in about 10 fold molar excess of streptavidin to biotinylated phosphatidylethanolamine.

19. A method for preparing a protein-coupled streptavidin-biotinylated phosphatidylethanolamine-containing liposome wherein streptavidin is non-covalently coupled to the liposome, comprising the steps of:
 (a) forming the streptavidin-coupled biotinylated phosphatidylethanolamine liposome of claim 13, and
 (b) incubating a biotinylated fluorescent-amine-labelled protein with the liposomes.

20. A composition comprising a protein coupled to streptavidin which is non-covalently coupled to a liposome comprising biotinylated phosphatidylethanolamine.

21. The composition of claim 20 wherein the liposome is a large unilamellar vesicle.

22. The composition of claim 20 wherein the protein is an immunoglobulin or a monoclonal antibody.

23. The composition of claim 22 wherein the immunoglobulin is Immunoglobulin G.

24. The composition of claim 20 additionally comprising a bioactive agent.

25. A pharmaceutical composition comprising the composition of claim 20 and a suitable pharmaceutical carrier or diluent.

* * * * *